United States Patent
Yang (10) Patent No.: US 9,616,056 B2
(45) Date of Patent: Apr. 11, 2017

(54) INHIBITION OF LEUKOTRIENE SYNTHESIS AND ACTIVITY IN THE TREATMENT OF SONIC HEDGEHOG-ASSOCIATED MEDULLOBLASTOMA

(71) Applicant: Institute for Cancer Research, Philadelphia, PA (US)

(72) Inventor: Zeng-Jie Yang, Huntingdon Valley, PA (US)

(73) Assignee: Institute for Cancer Research, Philadelphia, PA (US)

( * ) Notice: Subject to any disclaimer, the term of this patent is extended or adjusted under 35 U.S.C. 154(b) by 338 days.

(21) Appl. No.: 13/833,286

(22) Filed: Mar. 15, 2013

(65) Prior Publication Data
US 2014/0275162 A1  Sep. 18, 2014

(51) Int. Cl.
| | |
|---|---|
| A61K 31/47 | (2006.01) |
| A61K 31/381 | (2006.01) |
| A61K 31/404 | (2006.01) |
| A61K 31/405 | (2006.01) |
| A61K 31/00 | (2006.01) |

(52) U.S. Cl.
CPC .............. *A61K 31/47* (2013.01); *A61K 31/00* (2013.01); *A61K 31/381* (2013.01); *A61K 31/404* (2013.01); *A61K 31/405* (2013.01)

(58) Field of Classification Search
CPC .... A61K 31/00; A61K 31/381; A61K 31/404; A61K 31/405; A61K 31/47
See application file for complete search history.

(56) References Cited

U.S. PATENT DOCUMENTS

2011/0077305 A1* 3/2011 Jackson ................. 514/604

FOREIGN PATENT DOCUMENTS

WO      2008042896      4/2008

OTHER PUBLICATIONS

Rao et al. Oncogene, 2004, vol. 23, pp. 6156-6162.*
Yang, Z-J, et al., "Medulloblastoma can be Initiated by Deletion of patched in Lineage-Restricted Progenitors or Stem Cells", Cancer Cell., Aug. 12, 2008, 14(2):135-145.
Sahebjam, S., et al., "The Utility of Hedgehog Signaling Pathway Inhibition for Cancer", The Oncologist, 17, 2012, pp. 1090-1099.
Ohba, S., et al., "Patched1 Haploinsufficiency Increases Adult Bone Mass and Modulates Gli3 Repressor Activity", Developmental Cell, 14, May 2008, pp. 689-699.
Kimura, H., et al., "Transient Inhibition of the Hedgehog Pathway in Young Mice Causes Permanent Defects in Bone Structure", Cancerl Cell, 13, Mar. 2008, pp. 249-260.
Al-Nisiry, S., et al., "The use of Alamar Blue assay for quantitative analysis of viability, migration and invasion of choriocarcinoma cells", Human Reproduction, vol. 22, No. 5, Feb. 16, 2007, pp. 1304-1309.
Rubin, et al., "Targeting the Hedgehog pathway in cancer", Nat. Rev. Drug Disc., vol. 5, Dec. 2006, pp. 1026-1033.
Wang, B., et al., "An Inhibitor of Arachidonate 5-Lipoxygenace, Nordy, Induces Differentiation and Inhibits Self-Renewal of Glioma Stem-Like Cells", Stem Cell Rev. And Rep., Sep. 2010, pp. 1-13.
Kim, et al., "Effective Combination Therapy for Malignant Glioma with TRAIL—Secreting Mesenchymal Stem Cells and Lipoxygenase Inhibitor MK886", Can. Res., vol. 72, No. 18, Sep. 7, 2012, pp. 4807-4817.
Lim, et al., "MK886-induced apoptosis depends on the 5-L0 expression level in human malignant glioma cells", J. Neuro-Oncology, vol. 97, No. 3, Oct. 28, 2009, pp. 339-346.
Mangro, et al., "Down-regulation of vinculin upon MK886-induced apoptosis in LN18 glioblastoma cells", Neoplasma, vol. 54, No. 6, Jan. 1, 2007, pp. 517-526.
Ishii, et al., "5-lipoxygenase pathewy promotes cell proliferation in human glioma cell lines", Clinical Neuropathology, vol. 28, No. 6, Nov. 1, 2009, pp. 445-452.
Tang, et al., "Differential proliferative index of cancer stem-like cells in primary and recurrent medulloblastoma in human", Child's Nervous System, vol. 28, No. 11, Jul. 20, 2012, pp. 1869-1877.
Bijlsma, et al., "Sonic hedgehog induces transcription-independent cytoskeletal rearrangement and migration regulated by arachidonate metabolites", Cellular Signalling, vol. 19, No. 12, Oct. 9, 2007, pp. 2596-2604.
Dunn, et al., "Zafirlukast: An update of its pharmacology and therapeutic efficacy in asthma", Drugs, vol. 61, No. 2, Jan. 1, 2001, pp. 285-315.
"Zileuton. Leutrol (R) Zyflo (R)", Drugs of the Future, vol. 22, No. 7, Jul. 1, 1997, pp. 811-812.
International Search Report and Written Opinion for counterpart application PCT/US2014/025756 dated Sep. 9, 2014.
Yong, et al., "Emerging Interplay of Genetics and Epigenetics in Gliomas: A New Hope for Targeted Therapy", Semin Pediatr Neurol. Mar. 2015;22(1):14-22. doi: 10.1016/j.spen.2014.12.004. Epub Dec. 11, 2014.
Samkari, et al., "Medulloblastoma: Toward Biologically Based Management", Semin Pediatr Neurol. Mar. 2015;22 (1):6-13. doi: 10.1016/j.spen.2014.12.010. Epub Dec. 24, 2014.

* cited by examiner

*Primary Examiner* — Kara R McMillian
(74) *Attorney, Agent, or Firm* — Stadley Ronon Stevens & Young, LLP (57) ABSTRACT

Treating Sonic Hedgehog-Associated Medulloblastoma comprises inhibiting the synthesis or biologic activity of leukotrienes that drive Nestin expression in cancerous or precancerous granule neuron precursors and that further drive growth and proliferation of medulloblastoma cells through Nestin-mediated aberrant Sonic Hedgehog signaling.

26 Claims, 8 Drawing Sheets
(6 of 8 Drawing Sheet(s) Filed in Color)

INHIBITION OF LEUKOTRIENE SYNTHESIS AND ACTIVITY IN THE TREATMENT OF SONIC HEDGEHOG-ASSOCIATED MEDULLOBLASTOMA

REFERENCE TO A SEQUENCE LISTING

This application includes a Sequence Listing submitted electronically as a text file named MB_ST25.txt, created on Mar. 14, 2013 with a size of 1,000 bytes. The Sequence Listing is incorporated by reference herein.

FIELD OF THE INVENTION

The invention relates generally to the field of cancer treatment. More particularly, the invention relates to treatments for sonic hedgehog-associated medulloblastoma that target the biosynthesis and activity of leukotrienes in cancerous and precancerous, but not healthy, granule neuron precursors, with attendant inhibition of Nestin expression and/or aberrant sonic hedgehog signaling.

BACKGROUND OF THE INVENTION

Various publications, including patents, published applications, technical articles and scholarly articles are cited throughout the specification. Each of these cited publications is incorporated by reference herein, in its entirety and for all purposes.

Medulloblastoma is the most common malignant brain tumor in children. Despite the progress in the current tumor treatment, including surgery, chemotherapy and radiotherapy, more than 30% of medulloblastoma patients still die within 5 years after the diagnosis. Moreover, the survivors often suffer severe side effects of tumor treatment, including endocrine disorders, coordination problems and increased tumor incidence in other parts of the body. Therefore, improved strategies to treating medulloblastoma are highly needed.

Sonic hedgehog (Shh) signaling pathway plays a role in normal mammalian development, especially the proliferation of neuronal progenitors cells. Aberrant activation of this signaling is associated to the development of many malignancies including medulloblastoma, Basal cell carcinoma and rhabdomyosarcoma (Rubin, L L et al. (2006). Nat. Rev. Drug Discov. 5:1026-33). In studying the etiology of medulloblatoma, a conditional knockout mouse model (Math1-Cre/Ptch1$^{C/C}$ mice) was previously generated in which Patched1, an antagonist of Shh signaling, is deleted specifically in cerebellar granule neuron precursors (Yang Z J et al. (2008) Cancer Cell 14, 135-45). These animals develop tumors in their cerebellum, which resemble human medulloblastoma in their marker expression, cell morphology and genetic profiles. These studies have demonstrated that cerebellar GNPs represent cellular origin for medullobalstoma, and highlighted the importance of Shh signaling in the tumorigenesis of medulloblastoma.

Due to the role of Shh signaling in carcinogenesis, many Shh signaling inhibitors have been developed as potential anticancer agents (Sahebjam, S et al. (2012) Oncologist 17:1090-99.). The early data generated from these inhibitors held promise for some tumor types, especially in patients with Basal Cell Carcinoma. However, since the Shh pathway is required for normal development, severe on-target adverse effects of inhibiting the Shh pathway have been observed (Ohba, S. et al. (2008) Dev. Cell 14:689-99), which limits the suitability of such potential treatments. Indeed, it has been reported that transient inhibition of the Shh pathway in mice has resulted in permanent bone defects and altered growth, which persisted after cessation of the Shh pathway inhibitor and restoration of pathway (Kimura, H et al. (2008) Cancer Cell 13:249-60). This has greatly hampered the clinical application of general Shh pathway inhibitors in cancer treatment. Shh pathway inhibitors that selectively target tumor cells over healthy cells are needed.

SUMMARY OF THE INVENTION

The invention features methods for inhibiting Nestin expression in a cancerous or precancerous granule neuron precursor. The methods comprise inhibiting the synthesis or biologic activity of a leukotriene in the granule neuron precursor. Inhibiting the synthesis or biologic activity of a leukotriene may comprise one or more of contacting the granule neuron precursor with an agent that specifically inhibits the biologic activity of 5-lipoxygenase in an amount effective to specifically inhibit the biologic activity of 5-lipoxygenanse, contacting the granule neuron precursor with an agent that specifically inhibits the biologic activity of the 5-lipoxygenase activating protein in an amount effective to specifically inhibit the biologic activity of the 5-lipoxygenase activating protein, and/or contacting the granule neuron precursor with an agent that blocks the interaction of a leukotriene with the leukotriene receptor CysLT1 or CysLT2 in the granule neuron precursor in an amount effective to block the interaction of a leukotriene with the leukotriene receptor CysLT1 or CysLT2. Inhibiting the synthesis or biologic activity of the leukotriene inhibits Nestin expression in the granule neuron precursor.

The leukotriene is preferably a cysteinyl leukotriene. In some aspects, the leukotriene is leukotriene C4, leukotriene D4, and/or leukotriene E4.

The agent that specifically inhibits the expression or biologic activity of 5-lipoxygenase may comprise Zileuton (Formula III) or a pharmaceutically acceptable salt thereof. The agent that specifically inhibits the expression or biologic activity of the 5-lipoxygenase activating protein may comprise MK886 (Formula I) or a pharmaceutically acceptable salt thereof. The agent that blocks the interaction of a leukotriene with the leukotriene receptor CysLT1 or CysLT2 may comprise Montelukast (Formula II), Zafirlukast (Formula IV), a combination thereof, or a pharmaceutically acceptable salt of Montelukast or Zafirlukast.

The invention also features methods for treating Sonic Hedgehog-Associated Medulloblastoma. The invention also features methods for treating Glioblastoma Multiforme. Treating Sonic Hedgehog-Associated Medulloblastoma or treating Glioblastoma Multiforme may independently comprise administering to the brain of a subject in need thereof (a) an agent that specifically inhibits the biologic activity of 5-lipoxygenase in an amount effective to specifically inhibit the biologic activity of 5-lipoxygenanse, (b) an agent that specifically inhibits the biologic activity of the 5-lipoxygenase activating protein in an amount effective to specifically inhibit the biologic activity of the 5-lipoxygenase activating protein, or (c) an agent that blocks the interaction of a leukotriene with the leukotriene receptor CysLT1 or CysLT2 in an amount effective to block the interaction of a leukotriene with the leukotriene receptor CysLT1 or CysLT2. The leukotriene is preferably a cysteinyl leukotriene. In some aspects, the leukotriene is leukotriene C4, leukotriene D4, and/or leukotriene E4. The subject is preferably a human being.

In a method for treating Sonic Hedgehog-Associated Medulloblastoma, administering to the brain of the subject may comprise administering to a granule neuron precursor in the brain of the subject. In a method for treating Glioblastoma Multiforme administering to the brain of the subject may comprise administering to a glial cell in the brain of the subject. In preferred aspects, the granule neuron precursor or the glial cell expresses Nestin.

Inhibiting the biologic activity of 5-lipoxygenase and/or the biologic activity of 5-lipoxygenase activating protein in the granule neuron precursor or in the glial cell inhibits leukotriene synthesis, including synthesis of a cysteinyl leukotriene, and including synthesis of leukotriene C4, leukotriene D4, and/or leukotriene E4. Inhibiting leukotriene synthesis inhibits Nestin-mediated aberrant Sonic Hedgehog signaling in the granule neuron precursor or in the glial cell.

The agent that specifically inhibits the expression or biologic activity of 5-lipoxygenase may comprise Zileuton (Formula III) or a pharmaceutically acceptable salt thereof. The agent that specifically inhibits the expression or biologic activity of the 5-lipoxygenase activating protein may comprise MK886 (Formula I) or a pharmaceutically acceptable salt thereof. The agent that blocks the interaction of a leukotriene with the leukotriene receptor CysLT1 or CysLT2 may comprise Montelukast (Formula II), Zafirlukast (Formula IV), a combination thereof, or a pharmaceutically acceptable salt of Montelukast or Zafirlukast.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows Hematoxylin and Eosin staining of tumor sections prepared from Math1-Cre/Ptch1$^{C/C}$ animals at 8 weeks of age. FIG. 1B shows tumor sections in A (in frame) were immunostained for Nestin (in red). FIG. 1C shows sections from human medulloblastoma were analyzed for Nestin expression by immunohistochemistry (in red).

DETAILED DESCRIPTION OF THE INVENTION

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

MK886 (1-[(4-Chlorophenyl)methyl]-3-[(1,1-dimethylethyl)thio]-α,α-dimethyl-5-(1-methylethyl)-1H-Indole-2-propanoic acid) comprises a compound having Formula I, and all pharmaceutically acceptable salts thereof. Formula I:

Montelukast ((R,E)-2-(1-(((1-(3-(2-(7-chloroquinolin-2-yl)vinyl)phenyl)-3-(2-(2-hydroxypropan-2-yl)phenyl)propylthio)methyl)cyclopropyl)acetic acid) comprises a compound having Formula II, and all pharmaceutically acceptable salts thereof. Formula II:

Zileuton ((±)-1(1-Benzo[b]thien-2-ylethyl)-1-hydroxyurea) comprises a compound having Formula III, and all pharmaceutically acceptable salts thereof. Formula III:

Zafirlukast (cyclopentyl 3-{2-methoxy-4-[(o-tolylsulfonyl)carbamoyl]benzyl}-1-methyl-1H-indol-5-ylcarbamate) comprises a compound having Formula IV, and all pharmaceutically acceptable salts thereof. Formula IV:

Pharmaceutically acceptable salts of Formula I, Formula II, Formula III, or Formula IV may be acid or base salts. Non-limiting examples of pharmaceutically acceptable salts include sulfates, methosulfates, methanesulfates, pyrosulfates, bisulfates, sulfites, bisulfites, nitrates, besylates, phosphates, monohydrogenphosphates, dihydrogenphosphates, metaphosphates, pyrophosphates, chlorides, bromides, iodides, fluorides, acetates, propionates, decanoates, caprylates, acrylates, formates, isobutyrates, caproates, heptanoates, propiolates, oxalates, malonates, succinates, suberates, sebacates, fumarates, maleates, dioates, benzoates, chlorobenzoates, methylbenzoates, dinitromenzoates, hydroxybenzoates, methoxybenzoates, phthalates, sulfonates, toluenesulfonates, xylenesulfonates, pheylacetates, phenylpropionates, phenylbutyrates, citrates, lactates, γ-hydroxybutyrates, glycollates, tartrates, methanesulfonates, propanesulfonates, mandelates, and other salts customarily used or otherwise U.S. FDA-approved.

Inhibiting or interfering includes reducing, decreasing, blocking, preventing, delaying, inactivating, desensitizing, stopping, knocking down (e.g., knockdown), and/or down-regulating the biologic activity or expression of a molecule or pathway of interest. By way of example, but not of limitation, inhibiting the biologic activity of a lipoxygenase may include inhibiting the ability of the lipoxygenase to catalyze the dioxygenation of fatty acids into leukotrienes.

It has been observed in accordance with the invention that Nestin expression facilitates tumor cell development and proliferation in Sonic Hedgehog-Associated Medulloblastoma, particularly for granule neuron precursor cells. It has also been observed that Sonic Hedgehog signaling is necessary, but not sufficient, for this Nestin expression, and that leukotriene is a required co-partner of Sonic Hedgehog signaling to drive Nestin expression. Moreover, once expressed, Nestin drives aberrant Sonic Hedgehog-mediated signaling that further contributes to tumor progression. It has also been observed that inhibiting leukotriene synthesis or blocking leukotriene interaction with its receptors CysLT1 and CysLT2 inhibits Nestin expression in Medulloblastoma tumor cells, which in turn, inhibits their proliferation. This inhibition of proliferation was found to be specific to tumor cells, and that normal proliferation of healthy cells was not affected by targeting of leukotriene synthesis or interaction with its receptors. Accordingly, the invention features methods for treating Sonic Hedgehog-Associated Medulloblastoma by targeting the production or biologic activity of leukotrienes in granule neuron precursor cells. These methods may also be used to treat Glioblastoma. Any of the methods may be carried out in vivo, in vitro, or in situ.

The terms subject and patient are used interchangeably. A subject may be any organism, including mammals such as farm animals (e.g., horse, cow, sheep, pig), laboratory animals (e.g., mouse, rat, rabbit), companion animals (e.g., dog, cat), and non-human primates (e.g., new world monkey and old world monkey). In preferred aspects, the subject is a human being.

The invention features methods for inhibiting Nestin expression in a granule neuron precursor or in a glial cell. Preferably, the granule neuron precursor or glial cell expresses Nestin. In this regard, it is believed that only cancerous or precancerous granule neuron precursors (e.g., those that are, or will progress into, Sonic hedgehog-Associated Medulloblastoma tumor cells) and glial cells (e.g., those that are, or will progress into, Glioblastoma Multiforme cells) express Nestin, and that healthy granule neuron precursors (e.g., those that are not and will not progress into Sonic hedgehog-Associated Medulloblastoma tumor cells) and healthy mature glial cells (e.g., those that are not and will not progress into Glioblastoma Multiforme tumor cells) do not express Nestin. Thus, the methods may be applied to cancerous or precancerous (Sonic hedgehog-Associated Medulloblastoma) granule neuron precursors, but not healthy granule neuron precursors. As well, the methods may be applied to cancerous or precancerous (Glioblastoma Multiforme) glial cells, but not healthy glial cells. The granule neuron precursor and glial cells may be in the brain of a subject.

In general, the methods for inhibiting Nestin expression comprise inhibiting the synthesis or biologic activity of a leukotriene in the granule neuron precursor or in the glial cells. The leukotriene preferably is a cysteinyl leukotriene. In some preferred aspects, the cysteinyl leukotriene is leukotriene C4, leukotriene D4, or leukotriene E4, or any combination thereof.

Inhibiting the synthesis of a leukotriene may comprise contacting the granule neuron precursor or contacting the glial cell with an agent that specifically inhibits the expression or the biologic activity of 5-lipoxygenase, preferably using an amount of the agent effective to specifically inhibit the expression or the biologic activity of 5-lipoxygenase. Specifically inhibiting the expression or the biologic activity of 5-lipoxygenase comprises inhibiting the expression or biologic activity of 5-lipoxygenase to the exclusion of substantially all other lipoxygenase enzymes. Specific inhibition of the expression or biologic activity of 5-lipoxygenase includes inhibition of the expression or biologic activity of 5-lipoxygenase without significant inhibition of the expression or biologic activity of other lipoxygenase enzymes. The biologic activity of 5-lipoxygenase includes the biosynthesis of leukotriene C4, leukotriene D4, and/or leukotriene E4 from a fatty acid.

Inhibiting the synthesis of a leukotriene may comprise contacting the granule neuron precursor or the glial cell with an agent that specifically inhibits the expression or the biologic activity of the 5-lipoxygenase activating protein (FLAP), preferably using an amount effective to specifically inhibit the expression or the biologic activity of FLAP. Specifically inhibiting the expression or biologic activity of FLAP comprises inhibiting the expression or biologic activity of FLAP substantially to the exclusion of substantially all other 5-lipoxygenase activating proteins. Specific inhibition of the expression or biologic activity of FLAP includes inhibition of the expression or biologic activity of FLAP without significant inhibition of the expression or biologic activity of other 5-lipoxygenase activating proteins. The biologic activity of FLAP includes activation of 5-lipoxygenase toward synthesis of leukotriene C4, leukotriene D4, and/or leukotriene E4 from a fatty acid.

Inhibiting the biologic activity of a leukotriene may comprise contacting the granule neuron precursor or the glial cell with an agent that blocks the interaction of a leukotriene with a leukotriene receptor in the granule neuron precursor, preferably using an amount of the agent effective to block the interaction of the leukotriene with the leukotriene receptor. The leukotriene receptor is preferably CysLT1 or CysLT2. The agent preferably may freely cross the blood brain barrier. The biologic activity of a leukotriene includes any cell signaling or metabolism that is caused or facilitated by the leukotriene interacting with its receptor.

The agent that specifically inhibits the expression or biologic activity of 5-lipoxygenase may comprise Zileuton (Formula III) or a pharmaceutically acceptable salt thereof. The agent that specifically inhibits the expression or biologic activity of the 5-lipoxygenase activating protein may comprise MK886 (Formula I) or a pharmaceutically acceptable salt thereof. The agent that blocks the interaction of a leukotriene with the leukotriene receptor CysLT1 or CysLT2 may comprises Montelukast (Formula II), Zafirlukast (Formula IV), or a pharmaceutically acceptable salt of Montelukast or Zafirlukast. In a method for inhibiting Nestin expression, these agents (Formula I, Formula II, Formula III, and Formula IV) may be used individually or in any combination, e.g., Zileuton in combination with Zafirlukast, or Zileuton in combination with Montelukast.

Inhibiting Nestin expression in the granule neuron precursor or the glial cell may induce death in the granule neuron precursor or the glial cell, and may also inhibit growth and inhibit proliferation of the granule neuron precursor or the glial cell. It is believed that since healthy granule neuron precursors and healthy mature glial cells do not express Nestin, contacting healthy granule neuron precursors or glial cells with an agent that inhibits the expression or the biologic activity of 5-lipoxygenase, or inhibits the expression or the biologic activity of FLAP, or that blocks the interaction of a leukotriene with a leukotriene receptor will not induce death in a healthy granule neuron precursor or glial cell, and will not inhibit normal growth or normal proliferation of a healthy granule neuron precursor or glial cell, and will not inhibit differentiation of the granule neuron precursor into a granule neuron or glial cell.

The invention features methods for treating Sonic Hedgehog-Associated Medulloblastoma, and also for treating Glioblastoma Multiforme. In some aspects, the methods comprise administering to, preferably to the brain of, a subject in need thereof an agent that specifically inhibits the biologic activity of 5-lipoxygenase in an amount effective to specifically inhibit the biologic activity of 5-lipoxygenase. In some aspects, the methods comprise administering to, preferably to the brain of, a subject in need thereof an agent that specifically inhibits the biologic activity of the 5-lipoxygenase activating protein in an amount effective to specifically inhibit the biologic activity of the 5-lipoxygenase activating protein. In some aspects, the methods comprise administering to, preferably to the brain of, a subject in need thereof an agent that blocks the interaction of a leukotriene with the leukotriene receptor CysLT1 or CysLT2 in an amount effective to block the interaction of a leukotriene with the leukotriene receptor CysLT1 or CysLT2. The subject is preferably a human being.

In treating Sonic Hedgehog-Associated Medulloblastoma or treating Glioblastoma Multiforme according to such administering steps, one or more of the following occurs: Leukotriene synthesis, including leukotriene C4, D4, and/or E4, is inhibited in medulloblastoma or glioblastoma cells, but not healthy cells; Nestin expression is inhibited in medulloblastoma or glioblastoma cells that express Nestin, but not healthy cells that express Nestin; proliferation of medulloblastoma cells or glioblastoma cells is inhibited, but proliferation of healthy cells is not inhibited; growth of medulloblastoma cells or glioblastoma cells is inhibited, but growth of healthy cells is not inhibited; and/or aberrant Sonic Hedgehog signaling, particularly such signaling that is driven, at least in part, by Nestin, is inhibited, but normal Sonic Hedgehog signaling is not inhibited. Any such inhibition may result from one or more of inhibiting the expression or the biologic activity of 5-lipoxygenase in medulloblastoma cells, inhibiting the expression or the biologic activity of five lipoxygenase activating protein (FLAP), or blocking the binding or interaction of leukotriene (e.g., cysteinyl leukotriene such as leukotriene C4, D4, and/or E4) with the leukotriene receptor CysLT1 and/or Cys LT2. Medulloblastoma cells may be cancerous or precancerous granule neuron precursors. Glioblastoma cells may be cancerous or precancerous glial cells.

As the agents are intended to be administered to the brain, the agents preferably freely pass the blood brain barrier. The agents are preferably administered to granule neuron precursors in the brain to treat Sonic Hedgehog-Associated Medulloblastoma. The agents are preferably administered to glial cells in the brain to treat Glioblastoma Multiforme. The agents may be administered according to any methodology or route that is suitable for allowing the agents to reach their targeted cells. Administration may be passive or guided. Administration may be directly at/to the site of the tumor, or may be distal to the tumor, with diffusion and blood flow delivering the agent the appropriate site.

The agent that specifically inhibits the expression or biologic activity of 5-lipoxygenase may comprise Zileuton (Formula III) or a pharmaceutically acceptable salt thereof. The agent that specifically inhibits the expression or biologic activity of the 5-lipoxygenase activating protein may comprise MK886 (Formula I) or a pharmaceutically acceptable salt thereof. The agent that blocks the interaction of a leukotriene with the leukotriene receptor CysLT1 or CysLT2 may comprises Montelukast (Formula II), Zafirlukast (Formula IV), or a pharmaceutically acceptable salt of Montelukast or Zafirlukast. In a method for treating Sonic Hedgehog-Associated Medulloblastoma, these agents (Formula I, Formula II, Formula III, and Formula IV) may be used individually or in any combination, e.g., Zileuton in combination with Zafirlukast, or Zileuton in combination with Montelukast.

In any of the methods described in this specification, an agent, including an agent that specifically inhibits the expression or inhibits the biologic activity of 5-lipoxygenase, an agent that specifically inhibits the expression or the biologic activity of the 5-lipoxygenase activating protein (FLAP), or an agent that blocks the interaction of a leukotriene with the leukotriene receptor CysLT1 or CysLT2, may be formulated as a composition, for example, with a carrier. The carrier is preferably a pharmaceutically acceptable carrier. Acceptable carriers include any that do not interfere with the biological activity of the agent, and preferably is not toxic to the subject to which it is administered.

The carrier may be an aqueous solution, such as water, saline, or alcohol, or a physiologically compatible buffer, such as Hanks's solution, Ringer's solution, or physiological saline buffer. The carrier may contain formulatory agents, such as suspending, stabilizing and/or dispersing agents. The carrier may include a nonaqueous vehicle such as a nonpolar alcohol or oil, including plant or vegetable-derived oils such as olive oil, cottonseed oil, corn oil, canola oil, sesame oil, and other non-toxic oils.

The compositions may also be formulated in sustained release vehicles or depot preparations. For example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes, micelles, and emulsions are well-known examples of such delivery vehicles.

An effective amount of any given agent may comprise from about 0.01 µM to about 1 mM of the agent. An effective amount may comprise from about 0.1 µM to about 500 µM. An effective amount may comprise from about 0.1 µM to about 100 µM. An effective amount may comprise from about 0.1 µM to about 50 µM. An effective amount may comprise from about 0.1 µM to about 5 µM. An effective amount may comprise from about 0.1 µM to about 3 µM. An effective amount may comprise from about 0.1 µM to about 1 µM. An effective amount may comprise from about 0.1 µM to about 2.5 µM. An effective amount may comprise from about 1 µM to about 2.5 µM. An effective amount may comprise from about 1 µM to about 5 µM. An effective amount may comprise from about 2.5 µM to about 5 µM. An effective amount may comprise from about 0.5 µM to about 1 µM. An effective amount may comprise from about 0.5 µM to about 1.5 µM. An effective amount may comprise from about 0.6 µM to about 0.8 µM. An effective amount may comprise at least about 0.75 µM. An effective amount may comprise at least about 1 µM. An effective amount may comprise at least about 2 µM. An effective amount may comprise at least about 2.5 µM. An effective amount may comprise at least about 4 µM. An effective amount may comprise at least about 5 µM. The µM concentration may be determined according to any suitable method, and may constitute the concentration in the blood of a subject, or in the macro-environment of the tumor, or in the micro-environment of the tumor, or in the micro-environment of cells of the tumor. It is to be understood, however, that the concentration may vary depending on the cell type, tumor type, tumor location, tumor size, physical characteristics of the subject (species, age, height, weight, gender, among others).

The invention also features kits for practicing any of the methods described or exemplified herein. The kits comprise one or more of an agent that specifically inhibits the expression or the biologic activity of 5-lipoxygenase, an agent that specifically inhibits the expression or the biologic activity of the 5-lipoxygenase activating protein, and/or an agent that blocks the interaction of a leukotriene with the leukotriene receptor CysLT1 and/or CysLT2, and instructions for using the agent(s) in a method for treating Sonic Hedgehog-Associated Medulloblastoma, a method for inhibiting Nestin expression in a granule neuron precursor, or in a method for treating Glioblastoma Multiforme. The agent(s) may be in a composition comprising a pharmaceutically acceptable carrier. The agent(s) may be present in the kit in an amount effective for specifically inhibiting the expression or the biologic activity of 5-lipoxygenase, an amount effective for specifically inhibiting the expression or the biologic activity of the 5-lipoxygenase activating protein, or an amount effective to block the interaction of the leukotriene with the receptor CysLT1 and/or CysLT1. The agent that specifically inhibits the expression or biologic activity of 5-lipoxygenase may comprise Zileuton (Formula III) or a pharmaceutically acceptable salt thereof. The agent that specifically inhibits the expression or biologic activity of the 5-lipoxygenase activating protein may comprise MK886 (Formula I) or a pharmaceutically acceptable salt thereof. The agent that blocks the interaction of a leukotriene with the leukotriene receptor CysLT1 or CysLT2 may comprises Montelukast (Formula II), Zafirlukast (Formula IV), or a pharmaceutically acceptable salt of Montelukast or Zafirlukast.

The following examples are provided to describe the invention in greater detail. They are intended to illustrate, not to limit, the invention.

Example 1

Nestin Protein is Present on Medulloblastoma Cells

Nestin, a type VI intermediate filament protein, is considered to be a maker of neuronal stem and progenitor cells, although its expression is also found in other cell types including skeletal muscles, bone marrow stromal cells, pancreatic islet cells, hepatic cells and renal progenitors. In addition, Nestin expression has been detected in many types of neurogenic tumors including neuronal tumors, astrocytic tumors, oligodendroglial tumors, ependymal tumors, as well as in tumors of different origins, e.g., melanoma, pancreatic adenocarcinoma, breast tumors, and ovarian tumors. Although a high correlation between Nestin expression and cell proliferation has been demonstrated, the exact functions of Nestin still remain unresolved.

Figure 1:
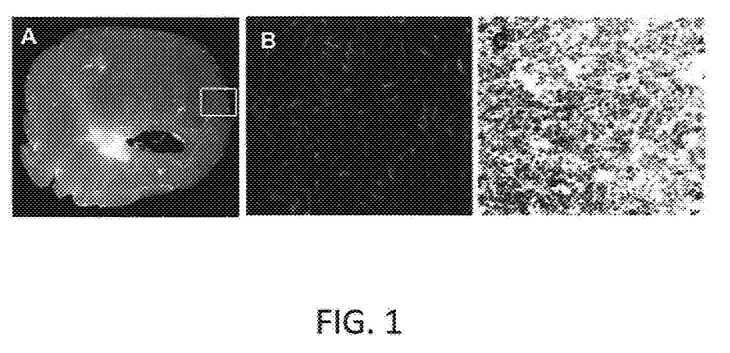
FIG. 1 shows Nestin expression in medulloblastoma cells.

To examine Nestin expression in medulloblastoma, medulloblastoma prepared from Math1-Cre/Ptch1$^{C/C}$ animals (FIG. 1A) was sectioned and immunostained with an antibody against the Nestin protein. As shown in FIG. 1B, Nestin is highly expressed in medulloblastoma. Moreover, extensive Nestin expression was also found in human medulloblastoma based on immunohistochemical analysis (FIG. 1C). However, no Nestin expression was detected among cerebellar granule neuron precursor (GNP) cells, the cell of origin for medulobalstoma (data not shown). These data suggest that Nestin is only expressed in tumor cells, but not in normal GNPs.

Example 2

Nestin is Critical for the Progression of Medulloblastoma Cells

To test the possible function of Nestin in tumor cell proliferation, tumor cells were isolated from Math1-Cre/

Figure 2:
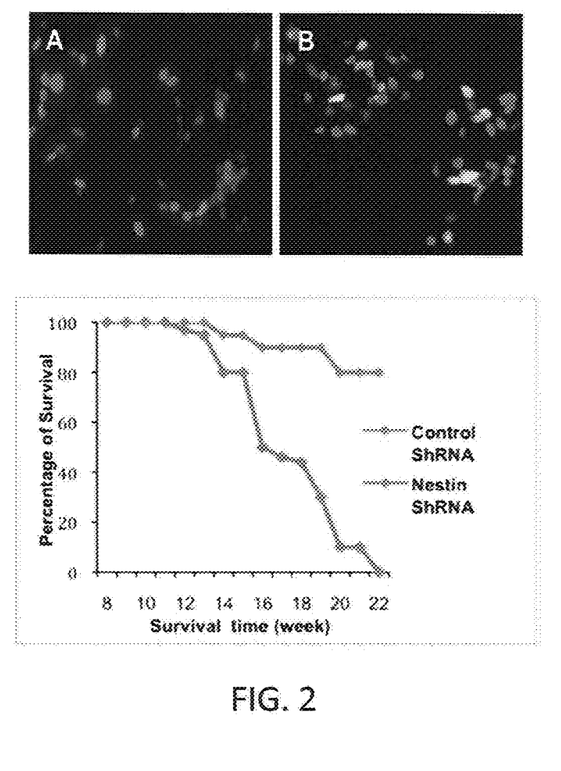
FIG. 2 shows Nestin is required for tumor cell proliferation. At 48 hrs after infection using lentivirus with Nestin shRNA (A, RFP tagged, in red) and scramble shRNA (B, RFP tagged, in red), tumor cells were harvested for immunostaining for Ki67 (in green). The survival curve of CB17SCID animals after the transplantation with tumor cells infected by lentiviruses carrying Nestin shRNA and scramble shRNA is shown.

Ptch1$^{C/C}$ animals, and the Nestin gene was deleted from tumor cells by infection with a lentivirus carrying Nestin shRNA (CCGGTCTGAGGCTCCCTATCCTAAACTC-GAGTTTAGGATAGGGAGCCTCAGATTTTTG; SEQ ID N0:1) or scramble shRNA (CCGGCAACAAGAT-GAAGAGCACCAACTCGAGTTGGTGCTCTTCATCTT-GTTGTTTTT; SEQ ID N0:2) as a control. As shown in FIG. 2, at 48 hrs following infection, no Nestin-deficient tumor cells were positive for Ki67, a marker for cell proliferation. As a comparison, no significant change was observed in the proliferation among tumor cells infected with scramble shRNA. These data indicate that Nestin is necessary for tumor cell proliferation.

To further investigate the role of Nestin in tumor cell growth in vivo, tumor cells from Math1-Cre/Ptch1$^{C/C}$ were infected with lentiviruses carrying shRNA or scramble shRNA. Infected cells were then harvested at 48 hrs following the infection, and transplanted intracranially into the cerebellum of the immunocompromised animals (CB17SCID mice). As shown in FIG. 2, tumor cells with control infection causes tumor formation in CB17SCID animals with 100% penetration (median survival time=19.6 weeks). However, most CB17SCID animals failed to develop medulloblastoma following the transplantation with Nestin-deficient tumor cells (80% animals are tumor-free by 22 weeks).

Example 3

Nestin Expression Relies on Leukotriene Activity

Figure 3:
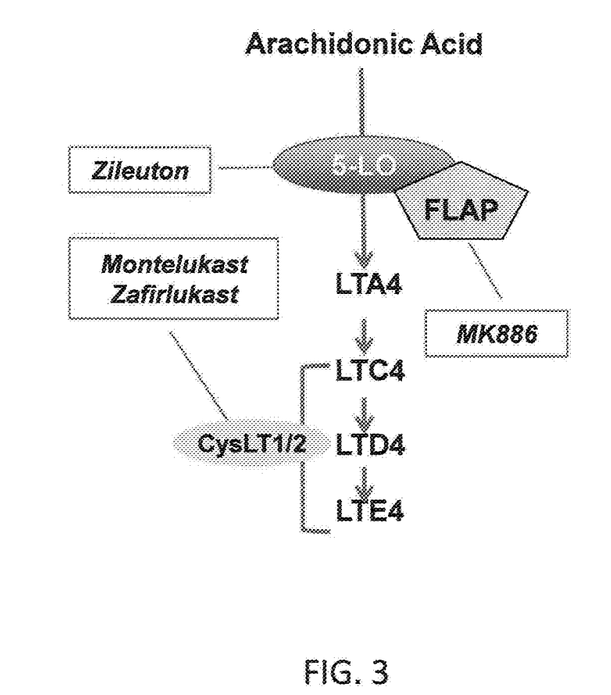
FIG. 3 shows the biosynthesis of leukotriene arachidonic acid is converted to LTA4 by 5-LO and FLAP. The stabilized leukotriene functions through two receptors: CysLT1/T2. Zileuton directly inhibits 5-LO activity, and MK886 effectively blocks FLAP functions. Montelukast and Zafirlukast are two potent inhibitors for leukotriene receptor.

Leukotriene C4 (LTC4), D4, and E4, collectively termed the cysteinyl leukotrienes (hereafter, referred to as leukotrienes), are peptide-conjugated lipids that are prominent products of activated eosinophils, basophils, mast cells, and macrophages. As shown in FIG. 3, leukotrienes are rapidly generated de novo from cell membrane phospholipid-associated arachidonic acid, which is liberated by cytosolic phospholipase A2 in response to cell activation.

Arachidonic acid is converted to an unstable intermediate, leukotriene A4 (LTA4), by the enzyme 5-lipoxygenase (5-LO). LTA4 is rapidly converted to more stable leukotriene C4 (LTC4), D4 (LTD4) and E4 (LTE4). 5-LO translocates from its cytosolic or nucleoplasmic location to the perinuclear envelope, where it acts in concert with 5-LO activating protein (FLAP), which is required for 5-LO to function enzymatically in intact cells. Leukotrienes exert their biological activities by binding to two distinct receptors: CysLT1 and CysLT2. Two main approaches have been developed to antagonize the activity of leukotriene: 1) inhibition of leukotriene synthesis, such as Zileuton that directly inhibits 5-LO, and MK886 that inhibits FLAP activity. 2) blockage of leukotriene receptors including Montelukast and Zafirlukast.

Leukotriene inhibitors have been already widely used in clinics for treating human asthma, and no severe side effects are reported so far. Originally identified on the basis of their contractile properties for intestinal and bronchial smooth muscle, they are now recognized as potent inflammatory mediators that initiate and propagate a diverse array of biologic responses. It has been reported that leukotriene is involved in Shh signaling-associated cytoskeletal rearrangement as well as neuronal migration.

Figure 4:
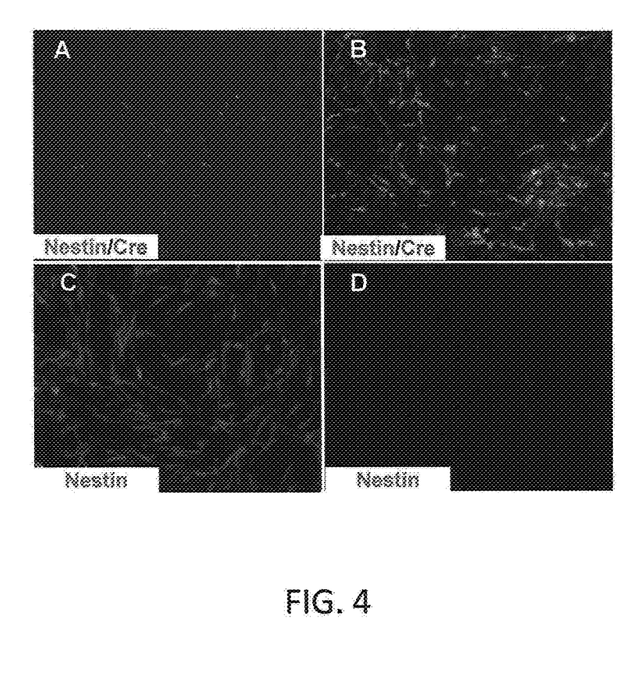
FIG. 4 shows Nestin expression in tumor cells relies on leukotriene synthesis. GNPs isolated from Ptch1$^{C/C}$ animals were plated and infected with lentivirus carrying Cre recombinase to delete Ptch1. At 48 hrs following the infection, GNPs were stained for Cre (green) and Nestin (red) in control (Panel A) and in the presence of 20 ng/ml leukotriene (Panel B). MB cells were plated in vitro for 48 hrs, and stained for Nestin (red) in control (Panel C) and in the presence of 5 μM MK886. (Panel D).

Since Nestin is a cytoskeleton protein, it was examined whether leukotriene could induce Nestin expression in medulloblastoma cells. For this purpose, cerebellar GNPs were isolated from Ptch1$^{C/C}$ animals, and Patched1 (Ptch1) was deleted from GNPs by using a lentivirus with Cre recombinase. At 48 hrs following the infection, cells were harvested to analyze Nestin expression by immunocytochemistry. As shown in FIG. 4, no Nestin expression was detected among GNPs after Ptch1 deletion, suggesting that activation of Shh signaling alone is not sufficient to induce Nestin expression in GNPs. However, in the presence of 20 ng/ml leukotriene, high level of Nestin protein was detected among Ptch1-deficient GNPs. The presence of Nestin mRNA and protein has been confirmed by RT-PCR and western blotting (data not shown). These data suggest that leukotriene is capable to stimulate Nestin expression in Ptc deficient GNPs.

To further examine whether Leukotriene synthesis is required for Nestin expression in tumor cells, tumor cells were isolated from the mouse model, which has already highly expresses Nestin in vivo, even in the culture at 48 hrs following plating. When the tumor cells were treated with MK886, a potent antagonist of 5-LO, Nestin expression among tumor cells was dramatically inhibited. These data indicate that Leukotriene is necessary for the initiation and maintenance of Nestin expression among medulloblastoma cells.

Example 4

Leukotriene Inhibition can Prevent Tumor Cell Proliferation

Figure 5:
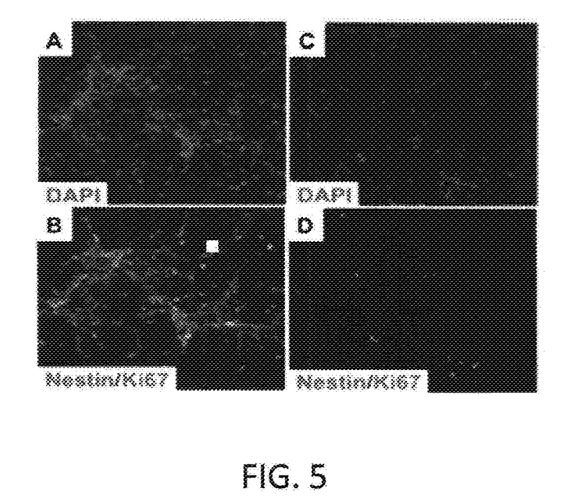
FIG. 5 shows MK886 inhibits tumor cell proliferation in vitro. Tumor cells isolated from Math1-Cre/Ptch1$^{C/C}$ animals, were treated with 3 μM DMSO (Panels A and B) or MK886 (Panels C and D) in vitro. After 48 hrs treatment, tumor cells were harvested for immunostaining with antibodies against Nestin (red) and Ki67 (green) (Panels B and D). The same cultures were counterstained by DAPI (blue) to show the total cell number (Panels A and B).

The studies described in the foregoing Examples suggest that Leukotriene is required for tumor cells to express Nestin, which is believed to be important for tumor cell proliferation. It was next investigated whether leukotriene inhibition can prevent tumor cell proliferation. For this purpose, endogeneous leukotriene activity in tumor cells was blocked by three different mechanisms: 1) inhibition of 5-LO (MK886 and NDGA); 2) inhibition of FLAP (Zileuton); 3) blockage of CysLT1 and CysLT2 (Montelukast, Zafirlukast). Tumor cells isolated from the mouse model were treated with MK886 or DMSO as a control. At 48 hrs after treatment, tumor cells were analyzed for proliferation by immunostaining for Ki67. As shown in FIG. 5, MK886 markedly inhibited Nestin expression in tumor cells, and prevented the proliferation among tumor cells. As a comparison, a significant proportion of tumor cells in control culture were still highly proliferative (Ki67 positive). These data suggest that tumor cells proliferation could be inhibited by blockage of leukotriene biosynthesis. Without intending to be limited to any particular theory or mechanism of action, it is believed that the above data also imply that leukotriene inhibitors prevent tumor cell proliferation through blockage of Nestin expression.

No Nestin expression was observed in wildtype GNPs, therefore, it was hypothesized that leukotriene inhibitors should have no effect on the proliferation of wildtype GNPs. To test this hypothesis and to compare the tumor inhibition between leukotriene inhibitors and cyclopamine, a common antagonist for Shh signaling, tumor cells and wildtype GNPs were treated with 5 µM MK886, 3 µg/ml cyclopamine, 10 µM NDGA, 20 µM Zileuton, 50 µM Montelukast and 50 µM Zafirlukast. DMSO was used as a negative control.

Figure 6:
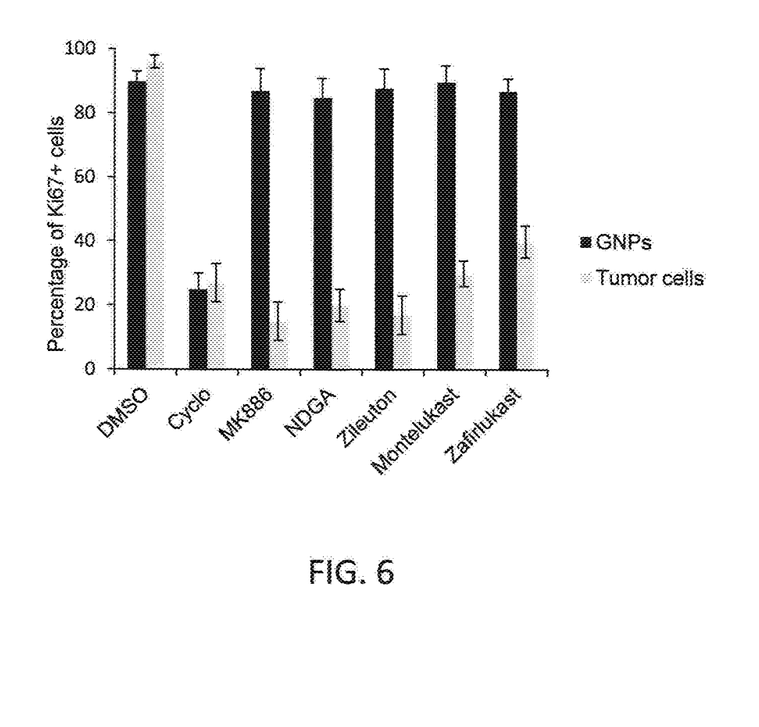
FIG. 6 shows leukotriene inhibitors prevent cell proliferation in a tumor cell specific manner. MB cells and normal GNPs were cultured and treated with 3 μM DMSO, 3 μg/ml Cyclopamine, 5 μM MK886, 10 μM NDGA, 20 μM Zileuton, 50 μM Montelukast and 50 μM Zafirlukast. 48 hrs later, the percentage of proliferating cells was calculated after immunostaining the culture with antibody against Ki67.

It is well established that sonic hedgehog protein is necessary for the in vivo and in vitro proliferation of normal GNPs. To maintain the in vitro proliferation of GNPs, 20 ng/ml recombinant Shh protein was added into the GNP culture. At 48 hrs after the treatment, cell cultures were harvested for measuring their proliferation by immunocytochemistry using Ki67 antibody. As shown in FIG. 6, both GNPs and tumor cells highly proliferate in vitro with DMSO. Consistent with previous reports, cyclopamine dramatically prevented the proliferation among both tumor cells and GNPs. However, all used leukotriene inhibitors markedly reduced tumor cell proliferation, but had no effect on GNP proliferation. These data suggest that leukotriene inhibitors can prohibit cell proliferation in a tumor cell-specific manner, leaving healthy cells alone.

Example 5

Tumor Growth can be Effectively Inhibited by Blocking Leukotriene Synthesis

Figure 7:
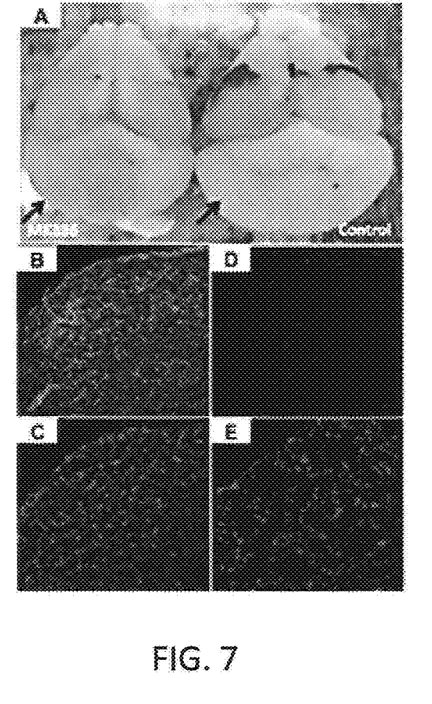
FIG. 7 shows MK886 inhibits in vivo tumor growth. Tumor bearing animals were treated with MK886 or DMSO by IP injection. After 1 month treatment, tumors were harvested. Tumor size was reduced by 30% with the treatment of MK886 (Panel A). After the treatment, tumors were sectioned for immunostaining for Nestin (Panels B and D), and Ki67 (Panels C and E). In the control (Panels B and C), tumor cells extensively express Nestin (Panel B) and all the tumor cells were Ki67 positive (Panel C). However, after MK886 treatment, nestin expression was dramatically reduced (Panel D), and only around 30% of tumor cells were still positive for Ki67 (Panel E).

Next, the efficacy of MK886 in inhibiting in vivo tumor growth was evaluated. Math1-Cre/Ptch1$^{C/C}$ animals at postnatal day 21 were treated daily with 30 μg MK886 by intraperitoneal injection. Three weeks later, tumor volume was evaluated by MRI imaging. As shown in FIG. 7, tumor size was significantly decreased (by over 30% in volume) after MK886 treatment, compared with that after control treatment (DMSO), suggesting that MK886 inhibits in vivo tumor progression.

Nestin expression and Ki67 was compared in tumor sections by immunohistochemical analysis. Extensive Nestin protein was found in the sections prepared from the DMSO treated tumor (FIG. 6B), whereas almost no Nestin is present in tumor after MK886 treatment (FIG. 6D). Similarly, based on Ki67 staining, the number of Ki67 positive cells decreased dramatically in tumor after MK886 treatment (FIG. 6E) compared with that in control (FIG. 6C). These data demonstrate the capacity of MK886 in inhibiting tumor growth in vivo.

Example 6

Gliblastoma Cells can Also be Inhibited by Leukotriene Inhibitors

Glioblastoma multiforme (GBM) is the most common tumor of the central nervous system. So far, standard of care includes surgical resection and radiotherapy with concomitant chemotherapy with temozolomide (TMZ) followed by 6 cycles of adjuvant chemotherapy with TMZ. Although about 10% of GBM patients showed long-term survival, GBM remains one of the most devastating malignancies with a median survival of 14.6 months.

Figure 8:
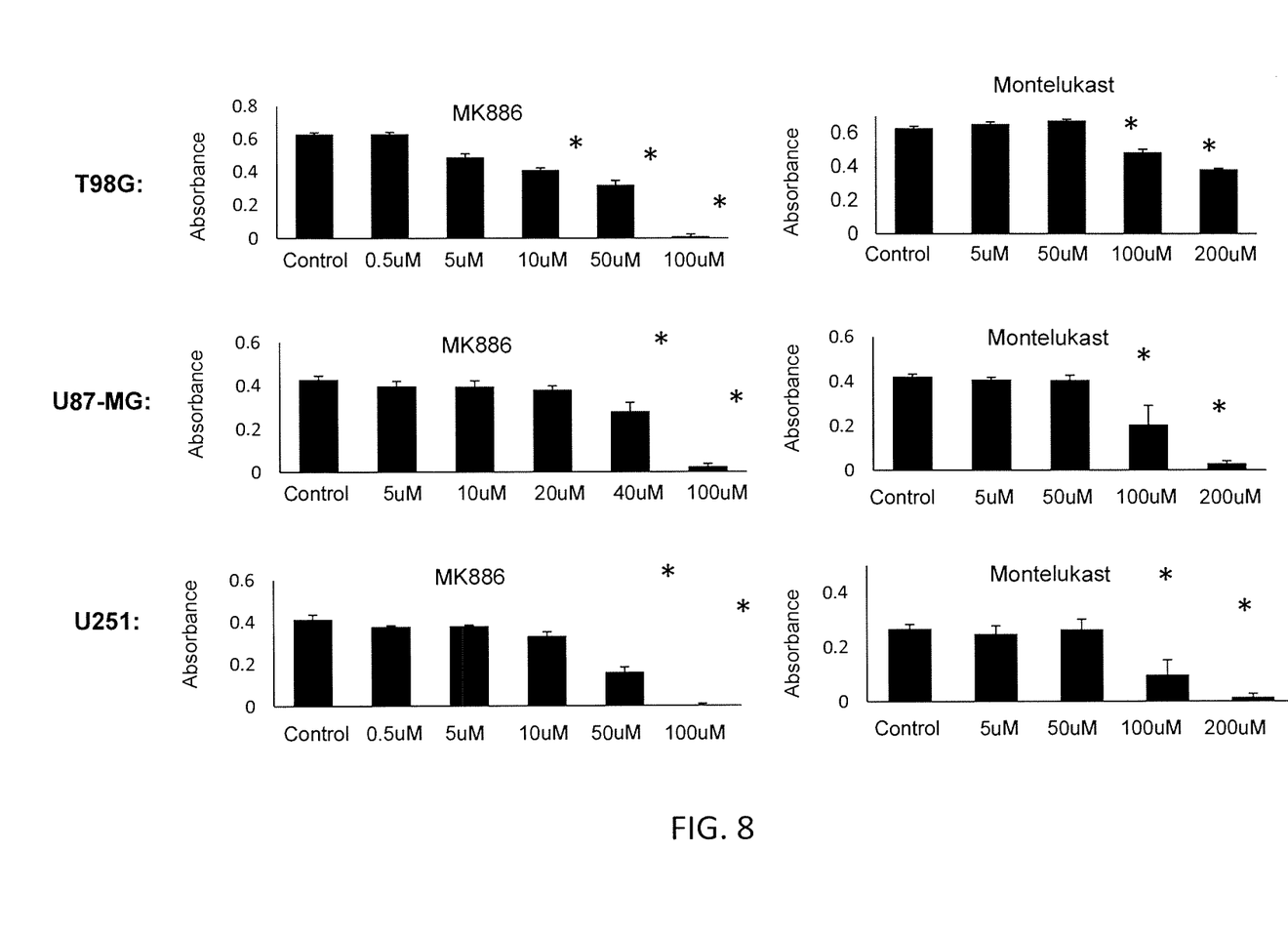
FIG. 8 shows survival of GBM cells after treatment with leukotriene inhibitors. Three GBM cell lines (T98G, U87-MG and U251) were plated and treated with MK886 and Montelukast at various concentrations for 48 hrs. Cell viability was measured by Alamar blue assay. Data represent the average of triplicate+SD. *p<0.05

To test the efficacy of leukotriene inhibitors in preventing glioblastoma cell proliferation, three GBM cell lines: T98G, U-87MG and U251 (purchased from an in-house cell culture facility) were utilized. The cell lines were treated with MK886 and Montelukast at different concentrations. After treatment for 48 hrs, cell survival and growth was analyzed by Alamar blue assay (Al-Nasiry, S et al. (2007) Hum. Reprod. 22:1304-9). As shown in FIG. 8, both MK886 and Montelukast can effectively reduce the viability of GBM cells. These data suggest that leukotriene inhibitor can also be utilized to treat GBM.

The invention is not limited to the embodiments described and exemplified above, but is capable of variation and modification within the scope of the appended claims.

I claim:

1. A method for treating Sonic Hedgehog-Associated Medulloblastoma, comprising administering to a subject in need thereof (a) an agent that inhibits the biologic activity of 5-lipoxygenase in an amount effective to inhibit the biologic activity of 5-lipoxygenanse in sonic hedgehog-associated medulloblastoma cells in the subject, (b) an agent that inhibits the biologic activity of the 5-lipoxygenase activating protein in an amount effective to inhibit the biologic activity of the 5-lipoxygenase activating protein in sonic hedgehog-associated medulloblastoma cells in the subject, or (c) an agent that blocks the interaction of a leukotriene with the leukotriene receptor CysLT1 or CysLT2 in an amount effective to block the interaction of a leukotriene with the leukotriene receptor CysLT1 or CysLT2 in sonic hedgehog-associated medulloblastoma cells in the subject, such that Sonic Hedgehog-Associated Medulloblastoma is treated in the subject.

2. The method of claim 1, wherein the sonic hedgehog-associated medulloblastoma cells express Nestin.

3. The method of claim 1, wherein inhibiting the biologic activity of 5-lipoxygenase in the sonic hedgehog-associated medulloblastoma cells inhibits proliferation or growth of the sonic hedgehog-associated medulloblastoma cells.

4. The method of claim 1, wherein inhibiting the biologic activity of the 5-lipoxygenase activating protein in the sonic hedgehog-associated medulloblastoma cells inhibits proliferation or growth of the sonic hedgehog-associated medulloblastoma cells.

5. The method of claim 1, wherein blocking the interaction of a leukotriene with the leukotriene receptor CysLT1 or CysLT2 in the sonic hedgehog-associated medulloblastoma cells inhibits proliferation or growth of the sonic hedgehog-associated medulloblastoma cells.

6. The method of claim 1, wherein the agent that specifically inhibits the expression or biologic activity of 5-lipoxygenase comprises Zileuton (Formula III) or a pharmaceutically acceptable salt thereof.

7. The method of claim 1, wherein the agent that specifically inhibits the expression or biologic activity of the 5-lipoxygenase activating protein comprises MK886 (Formula I) or a pharmaceutically acceptable salt thereof.

8. The method of claim 1, wherein the agent that blocks the interaction of a leukotriene with the leukotriene receptor CysLT1 or CysLT2 comprises Montelukast (Formula II) or Zafirlukast (Formula IV) or a pharmaceutically acceptable salt of Montelukast or Zafirlukast.

9. The method of claim 1, wherein the subject is a human being.

10. A method for treating Sonic Hedgehog-Associated Medulloblastoma, comprising administering to a subject in need thereof Zileuton (Formula III) or a pharmaceutically acceptable salt thereof in an amount effective to treat Sonic Hedgehog-Associated Medulloblastoma in the subject.

11. The method of claim 10, wherein the Zileuton (Formula III) or pharmaceutically acceptable salt thereof is administered to the brain of the subject.

12. The method of claim 10, wherein cells of the sonic hedgehog-associated medulloblastoma express Nestin.

13. The method of claim 10, wherein the Zileuton (Formula III) or pharmaceutically acceptable salt thereof inhibits proliferation or growth of sonic hedgehog-associated medulloblastoma cells.

14. The method of claim 10, wherein the subject is a human being.

15. A method for treating Sonic Hedgehog-Associated Medulloblastoma, comprising administering to a subject in need thereof Montelukast (Formula II), Zafirlukast (Formula IV), or a pharmaceutically acceptable salt thereof in an amount effective to treat Sonic Hedgehog-Associated Medulloblastoma in the subject.

16. The method of claim 15, wherein the Montelukast (Formula II), Zafirlukast (Formula IV), or pharmaceutically acceptable salt thereof is administered to the brain of the subject.

17. The method of claim 15, wherein cells of the sonic hedgehog-associated medulloblastoma express Nestin.

18. The method of claim 15, wherein the Montelukast (Formula II), Zafirlukast (Formula IV), or pharmaceutically acceptable salt thereof inhibits proliferation or growth of sonic hedgehog-associated medulloblastoma cells.

19. The method of claim 15, wherein the method comprises administering to the subject Montelukast (Formula II) or a pharmaceutically acceptable salt thereof in an amount effective to treat Sonic Hedgehog-Associated Medulloblastoma in the subject.

20. The method of claim 15, wherein the method comprises administering to the subject Zafirlukast (Formula IV) or a pharmaceutically acceptable salt thereof in an amount effective to treat Sonic Hedgehog-Associated Medulloblastoma in the subject.

21. The method of claim 15, wherein the subject is a human being.

22. A method for treating Sonic Hedgehog-Associated Medulloblastoma, comprising administering to a subject in need thereof MK886 (Formula I) or a pharmaceutically acceptable salt thereof in an amount effective to treat Sonic Hedgehog-Associated Medulloblastoma in the subject.

23. The method of claim 22, wherein the MK886 (Formula I) or pharmaceutically acceptable salt thereof is administered to the brain of the subject.

24. The method of claim 22, wherein cells of the sonic hedgehog-associated medulloblastoma express Nestin.

25. The method of claim 22, wherein the MK886 (Formula I) or pharmaceutically acceptable salt thereof inhibits proliferation or growth of sonic hedgehog-associated medulloblastoma cells.

26. The method of claim 22, wherein the subject is a human being.

* * * * *

UNITED STATES PATENT AND TRADEMARK OFFICE
CERTIFICATE OF CORRECTION

PATENT NO. : 9,616,056 B2
APPLICATION NO. : 13/833286
DATED : April 11, 2017
INVENTOR(S) : Zeng-Jie Yang It is certified that error appears in the above-identified patent and that said Letters Patent is hereby corrected as shown below:

In the Specification

In Column 1, immediately following the title of the application, the following Section Heading and paragraph should be inserted:
-- STATEMENT OF GOVERNMENT SUPPORT
This invention was made with government support under Grant No. CA178380 awarded by the National Institutes of Health. The government has certain rights in the invention. --

Signed and Sealed this
Second Day of October, 2018

Andrei Iancu
*Director of the United States Patent and Trademark Office*

SEQUENCE LISTING

```
<160> NUMBER OF SEQ ID NOS: 4

<210> SEQ ID NO 1
<211> LENGTH: 58
<212> TYPE: DNA
<213> ORGANISM: Homo sapiens

<400> SEQUENCE: 1
ccggtctgag gctccctatc ctaaactcga gtttaggata gggagcctca gatttttg      58

<210> SEQ ID NO 2
<211> LENGTH: 57
<212> TYPE: DNA
<213> ORGANISM: Homo sapiens

<400> SEQUENCE: 2
ccggcaacaa gatgaagagc accaactcga gttggtgctc ttcatcttgt tgtttt        57

<210> SEQ ID NO 3
<211> LENGTH: 58
<212> TYPE: RNA
<213> ORGANISM: Homo sapiens

<400> SEQUENCE: 3
ccggucugag gcucccuauc cuaaacucga guuuaggaua gggagccuca gauuuuug      58

<210> SEQ ID NO 4
<211> LENGTH: 57
<212> TYPE: RNA
<213> ORGANISM: Homo sapiens
```

```
<400> SEQUENCE: 4
ccggcaacaa gaugaagagc accaacucga guuggugcuc uucaucuugu uguuuuu      57
```